(12) United States Patent
Datta

(10) Patent No.: US 11,224,466 B2
(45) Date of Patent: Jan. 18, 2022

(54) DEVICES AND METHODS FOR TREATING SPINAL STRESS FRACTURES

(71) Applicant: Devin Datta, Merritt Island, FL (US)

(72) Inventor: Devin Datta, Merritt Island, FL (US)

( * ) Notice: Subject to any disclaimer, the term of this patent is extended or adjusted under 35 U.S.C. 154(b) by 0 days.

(21) Appl. No.: 16/872,773

(22) Filed: May 12, 2020

(65) Prior Publication Data

US 2020/0360061 A1 Nov. 19, 2020

Related U.S. Application Data

(60) Provisional application No. 62/846,814, filed on May 13, 2019.

(51) Int. Cl.
*A61B 17/70* (2006.01)

(52) U.S. Cl.
CPC ...... *A61B 17/7071* (2013.01); *A61B 17/7011* (2013.01); *A61B 17/7047* (2013.01)

(58) Field of Classification Search
CPC ............ A61B 17/7071; A61B 17/7056; A61B 17/7067; A61B 17/7011; A61B 17/7047
USPC ................. 606/246, 248, 276, 281
See application file for complete search history.

(56) References Cited

U.S. PATENT DOCUMENTS

| | | | |
|---|---|---|---|
| 8,043,337 B2 | 10/2011 | Klyce et al. | |
| 8,043,343 B2 | 10/2011 | Miller et al. | |
| 8,333,770 B2 | 12/2012 | Hua | |
| 8,496,685 B2 | 7/2013 | Landry et al. | |
| 8,608,780 B2 | 12/2013 | Forton et al. | |
| 8,721,691 B2 | 5/2014 | Hua | |
| 2006/0265069 A1* | 11/2006 | Goble | A61F 2/4405 623/17.11 |
| 2007/0083201 A1 | 4/2007 | Jones et al. | |
| 2008/0058806 A1 | 3/2008 | Klyce et al. | |
| 2008/0243186 A1* | 10/2008 | Abdou | A61B 17/7032 606/246 |
| 2008/0255619 A1* | 10/2008 | Schneiderman | A61B 17/7058 606/276 |
| 2009/0005818 A1* | 1/2009 | Chin | A61F 2/4405 606/247 |
| 2010/0274291 A1* | 10/2010 | McClellan, III | A61B 17/7004 606/276 |
| 2011/0178552 A1 | 7/2011 | Biscup et al. | |
| 2015/0196328 A1* | 7/2015 | Hirschl | A61B 17/7047 606/276 |

(Continued)

FOREIGN PATENT DOCUMENTS

KR 20070077762 7/2007

*Primary Examiner* — Eduardo C Robert
*Assistant Examiner* — David C Comstock
(74) *Attorney, Agent, or Firm* — Allen, Dyer, Doppelt + Gilchrist, PA

(57) ABSTRACT

A spinal stabilization system may include at least one pedicle screw comprising a threaded base to be connected to a superior pedicle of a vertebra and a screw head attached to the threaded base. The system may further include at least one pars interarticularis clamp comprising an elongate body defining a screw head connection point to be connected to the screw head of the pedicle screw, and a laminar hook coupled to the elongate body and configured to wrap around an edge of the lamina and compress the pars interarticularis of the vertebra when the screw head connection point is connected to the screw head.

12 Claims, 10 Drawing Sheets

(56) References Cited

U.S. PATENT DOCUMENTS

| | | | |
|---|---|---|---|
| 2015/0374416 A1* | 12/2015 | Warren | A61B 17/7001 |
| | | | 606/247 |
| 2016/0331410 A1* | 11/2016 | Tsuang | A61B 17/7037 |
| 2017/0100164 A1 | 4/2017 | Landry et al. | |
| 2017/0296239 A1* | 10/2017 | Cordaro | A61B 17/7059 |
| 2017/0340365 A1 | 11/2017 | Baynham | |
| 2018/0008321 A1* | 1/2018 | Stern | A61B 17/7056 |
| 2018/0008322 A1* | 1/2018 | Giordano | A61B 17/7059 |
| 2020/0253647 A1* | 8/2020 | White | A61B 17/7067 |

\* cited by examiner

DEVICES AND METHODS FOR TREATING SPINAL STRESS FRACTURES

CROSS-REFERENCE TO RELATED APPLICATIONS

This application claims the benefit of U.S. provisional application No. 62/846,814 filed May 13, 2019, which is hereby incorporated herein in its entirety by reference.

TECHNICAL FIELD

The present disclosure generally relates to devices and methods for the treatment of skeletal fractures, and more particularly spinal fractures.

BACKGROUND

One of the most common injuries seen in young athletes by back specialists are pars interarticularis fractures, also called spondylolysis. This is a sometimes acute or chronic fracture that occurs in the high stress zone between the superior and inferior facet joints at a motion segment, hence the term pars interarticularis (part between the joints). Typically, the injury occurs in athletes requiring increased hyperextension, such as gymnasts and football lineman, but also in any repetitive high intensity sport.

The usual treatment is bracing and rest for six to twelve weeks, then gradual resumption of the sport. During the rest period the fracture will either heal or will sometimes go on to a permanent chronic spondylolysis. Many patients with chronic spondylolysis can live pain free and relatively normal lives even with the defect, sometimes even returning to competitive sports. However, often these patients have to deal with chronic episodes of pain and re-injury. Many will eventually require spinal fusion years down the road if back or leg pain develops and persists.

A particular dilemma involves young athletes with continued pain and discomfort which, despite bracing, limits their ability to play a sport. Sometimes these patients are even bothered with simple daily activities. Many of these athletes have college and sometimes professional aspirations, and are looking for a way to return to full function without continued re-injury.

SUMMARY

A spinal stabilization system may include at least one pedicle screw comprising a threaded base to be connected to a superior pedicle of a vertebra and a screw head attached to the threaded base. The system may further include at least one pars interarticularis clamp comprising an elongate body defining a screw head connection point to be connected to the screw head of the pedicle screw, and a laminar hook coupled to the elongate body and configured to wrap around an edge of the lamina and compress the pars interarticularis of the vertebra when the screw head connection point is connected to the screw head.

In one example embodiment, the at least one pedicle screw may comprise first and second pedicle screws to be connected to opposing first and second superior pedicles of the vertebra, respectively, and the at least one pars interarticularis clamp may comprise a first pars interarticularis clamp coupled between the first pedicle screw and the edge of the lamina, and a second pars interarticularis clamp connected between the second pedicle screw and the edge of the lamina. Furthermore, the screw head connection point may be at a proximal end of the elongate body, and the laminar hook may be connected to a distal end of the elongate body opposite the proximal end.

In accordance with another example embodiment, the at least one pedicle screw may comprise first and second pedicle screws to be connected to opposing first and second superior pedicles of the vertebra, respectively. Moreover, the elongate body may comprise a curved body having a first end defining a first screw head connection point to be connected to the screw head of the first pedicle screw, and a second end defining a second screw head connection point to be connected to the screw head of the second pedicle screw. By way of example, the laminar hook may be coupled to a midpoint of the curved body. Also, the curved body may define a U-shape, for example. In accordance with an example implementation, the elongate body may comprise a flat body.

A related spinal stabilization device, similar to the one discussed briefly above, and spinal stabilization method are also provided. The method may include connecting a threaded base of a pedicle screw to a superior pedicle of a vertebra, the pedicle screw comprising a screw head attached to the threaded base. The method may further include connecting at least one pars interarticularis clamp comprising an elongate body and a laminar hook connected to the elongate body to the vertebra by wrapping the laminar hook around an edge of the lamina of the vertebra, and connecting a screw head connection point of the elongate body to the screw head of the pedicle screw to compress the pars interarticularis of the vertebra.

DETAILED DESCRIPTION

Figure 1:
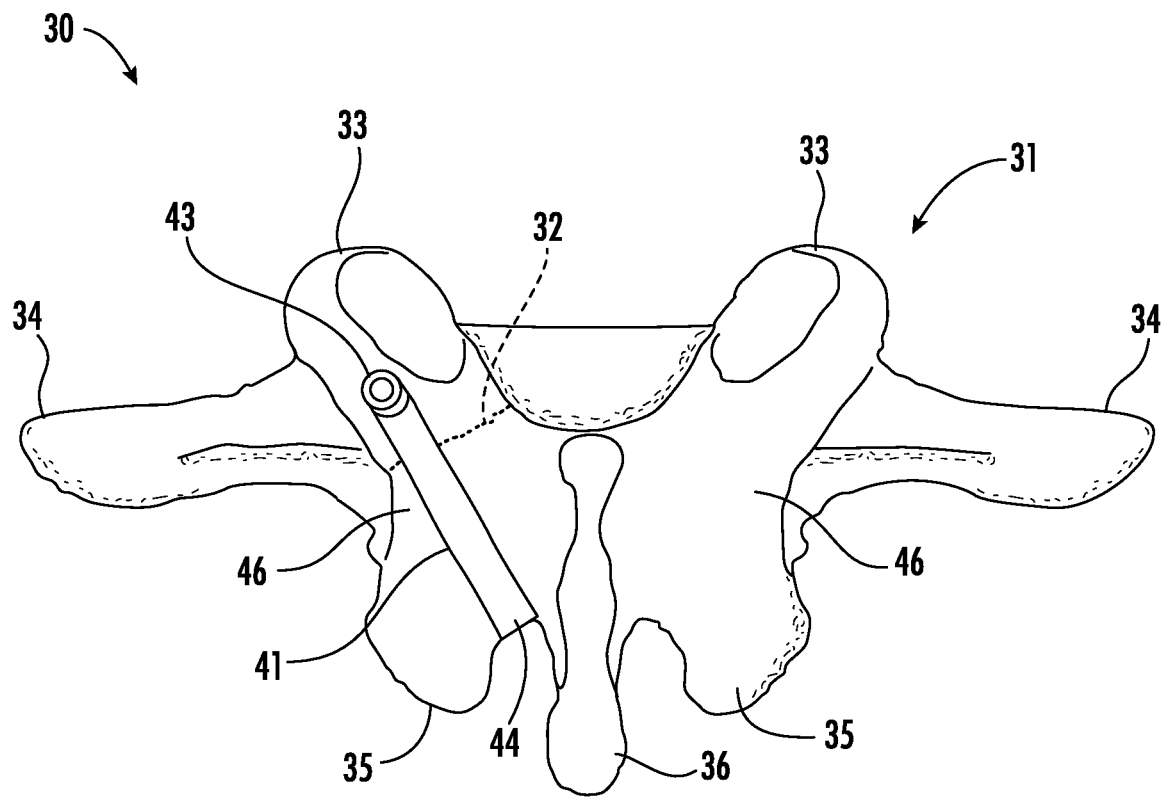
FIG. 1 is a schematic top view of a vertebra in which a spinal stabilization system has been installed in accordance with an example embodiment for the treatment of a pars interarticularis stress fracture.
Figure 2:
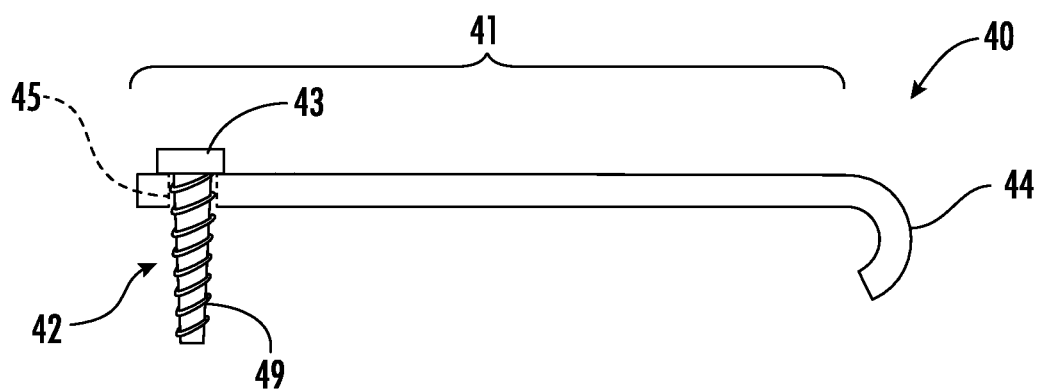
FIG. 2 is a side view of the pars interarticularis clamp of the system of FIG. 1.

The present description is made with reference to the accompanying drawings, in which exemplary embodiments are shown. However, many different embodiments may be used, and thus the description should not be construed as limited to the example embodiments set forth herein. Rather, these embodiments are provided so that this disclosure will be thorough and complete. Like numbers refer to like elements throughout, and prime number are used to indicate similar elements in different embodiments.

Referring initially to FIGS. 1-7, the present disclosure relates to a system 30 and associated methods for treating bone fractures, and in particular spinal fractures such as pars interarticularis or "pars" stress fractures 32 in a vertebra 31. In the illustrated examples, the pars stress fractures 32 are represented by dashed lines at the typical location where pars fractures occur. The vertebra 31 illustratively includes superior articulating processes 33, also referred to as superior pedicles, transverse processes 34, inferior articulating processes 35, and spinous process 36.

By way of background, as noted above the typical treatment for a pars stress fracture is immobilization with a back brace and several months of rest. In this typical pars fracture treatment scenario, after months or years of non-operative management, if pain persists the patient has the choice of activity modification (e.g., giving up certain sports/activities) or surgery. The conventional surgical treatment has been with relatively bulky spinal immobilization or fusion hardware that is not particularly well suited for pars fracture repair or stabilization. While this treatment may be met with some success, it is less than ideal in that it is relatively invasive, has a long recovery time, and results in loss of mobility as the vertebrae are fused together. Another potential approach is bone grafting and percutaneous stabilization across these fractures and motion segment. Yet, this requires hardware removal before breakage, and there is still a chance of re-injury despite going through this process. Results are variable, but often the patient can return in six to twelve months to the sport or desired activity.

The system 30 illustratively includes a pars interarticularis clamp 40, which is also referred to as a "pars clamp" herein. The pars clamp 40 is configured to stabilize the vertebral fracture 32 and allow direct "repair"/bone grafting. In the illustrated example, the pars clamp 40 includes an elongate body 41, a proximal end which is configured to be connected to the head 43 of a pedicle screw 42, which further includes a threaded base 49 coupled to the head. The head 43 and threaded base 49 may be integrally formed or a unitary body in some embodiments, and in other embodiments the head may be removably coupled to the threaded base (e.g., a ratcheting head, etc.) The proximal end of the pars clamp 40 has a hole or notch 45 therein for receiving the screw 42. A distal end of the pars clamp 40 opposite the proximal end terminates in a laminar hook 44. The laminar hook 44 may be integrally formed with the elongate body 41 as a unitary piece, for example, although it could also be a separate piece that screws in or otherwise gest fastened or coupled to the elongate body A minimally invasive surgical procedure may be used for installing the pars clamp 40 to advantageously help expedite the return of a patient to sports or other activities. This procedure involves using a small "cortical trajectory" screw 43 (or a more traditional trajectory screw, if desired) in the superior pedicle 33 just above the fracture 32 by connecting the laminar hook 44 to the lamina below the fracture. When the pars clamp is fastened in place by connecting the proximal end to the screw 42 under tension, this advantageously applies a compressional force to the pars interarticularis 46 across the fracture 32. This not only avoids spanning the motion segment of the vertebra 31, it also avoids the need for spinal fusion. That is, installation of the pars clamp 40 does not result in any loss of mobility between the vertebrae of the spine. The above-described surgical procedure can be done bilaterally through a 4-5 cm midline incision with no dissection past the pars or facet joint. In fact, neither facet joint needs exposure, as will be appreciated by those skilled in the art.

After the procedure, normal motion of the facets above and below the fixation may be restored because the fixation is confined to the fractured segment only. The pars clamp 40 is relatively low profile, and accordingly does not need to be removed. As such, the system 30 advantageously functions as an internal brace that not only applies compressional force to the fracture 32 to aid in healing, but it also may remain in the patient without discomfort or other associated complications to help provide continued stabilization and thereby prevent re-injury. In an example procedure, the patient may wear an external support brace for six weeks and then begin light core strengthening at six to twelve weeks post-op, although other time frames may be used as appropriate.

As a result, the above-described approach utilizing pars clamps 40 may provide a relatively quick, easy, reliable, and minimally invasive technique for treating pars fractures 32 as compared to current approaches. Moreover, it may also allow athletes or other patients the ability to return to sports in approximately three months, and more generally allow patients to return to regular activities quicker. Additionally, this approach allows direct treatment of the fracture 32 while maintaining normal motion of the joints above and below, and decreasing the chances that a spinal fusion will be required at a later time to treat chronic spondylolysis/spondylolisthesis.

In an example implementation, the screw head 43 may be poly-axial but configured to ratchet/compress and permanently lock as the laminar hook 40 end of the elongate body 40 compresses the pars interarticularis 46 and the fracture 32. In the illustrated example, the elongate body 41 is a flat bar, but in other implementations it may be a rod (e.g., cylindrical) or other shapes/geometries, for example.

Figure 3:
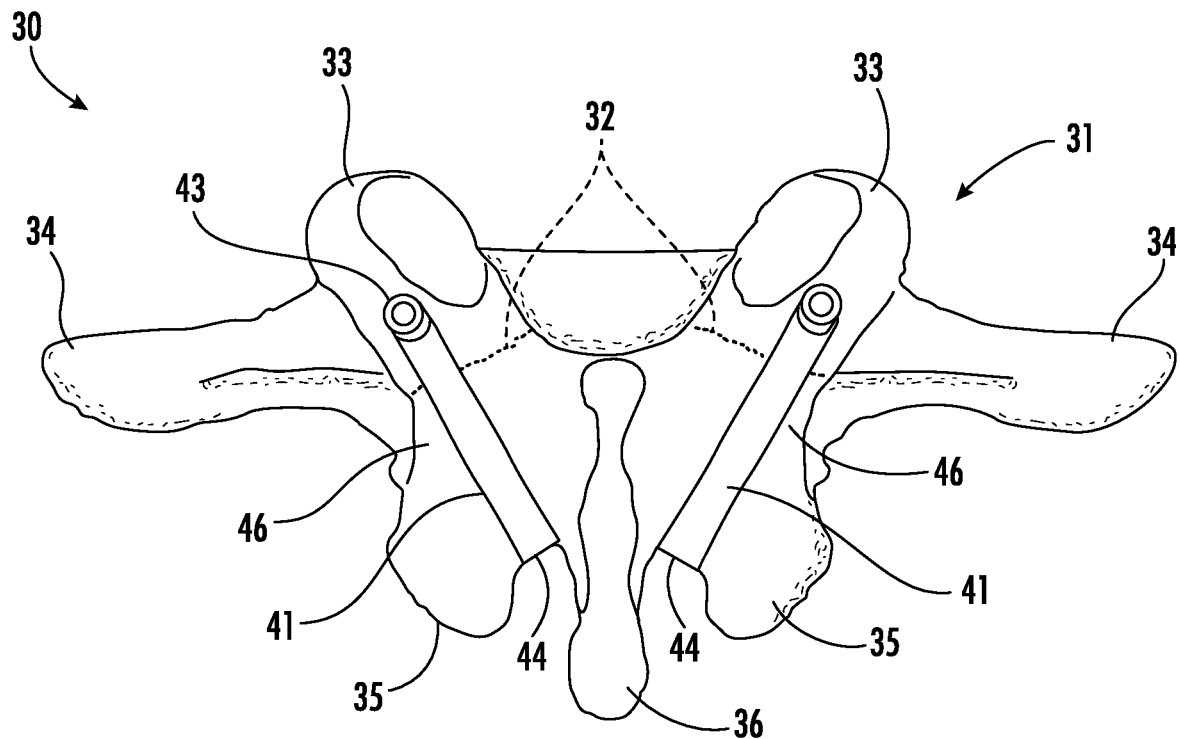
FIG. 3 is a schematic top view of another example configuration of the system of FIG. 1 in which a pair of pars interarticularis clamps have been installed in a vertebra.
Figure 4:
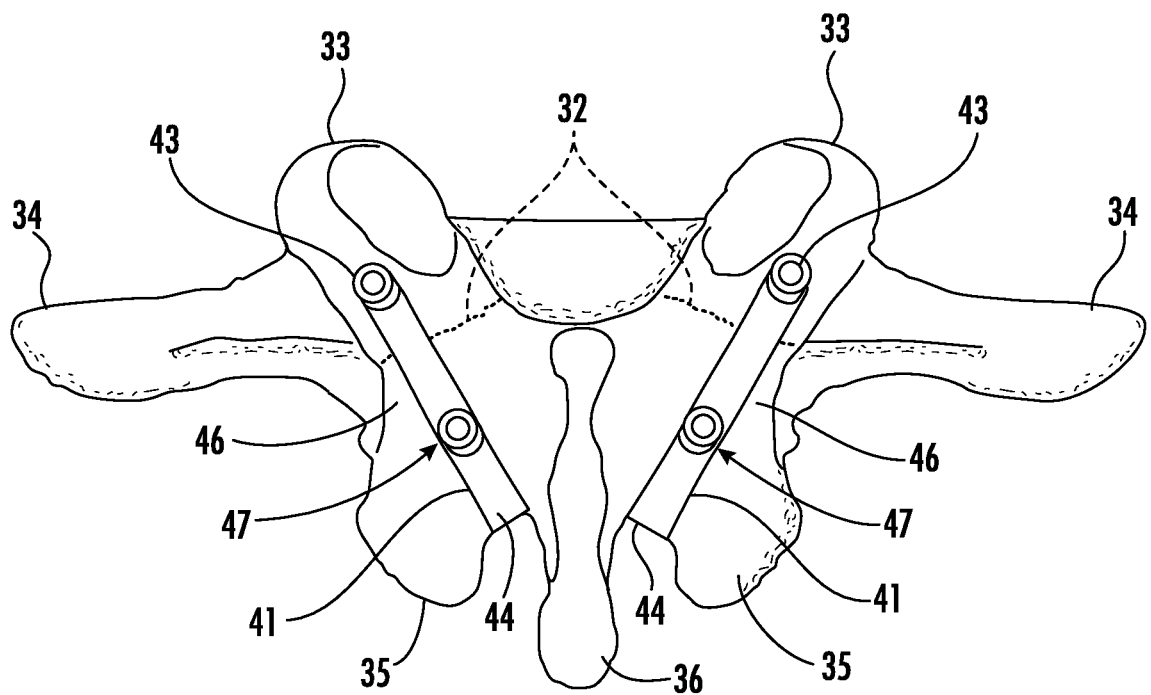
FIG. 4 is a schematic top view of another example implementation of the system of FIG. 3.
Figure 5:
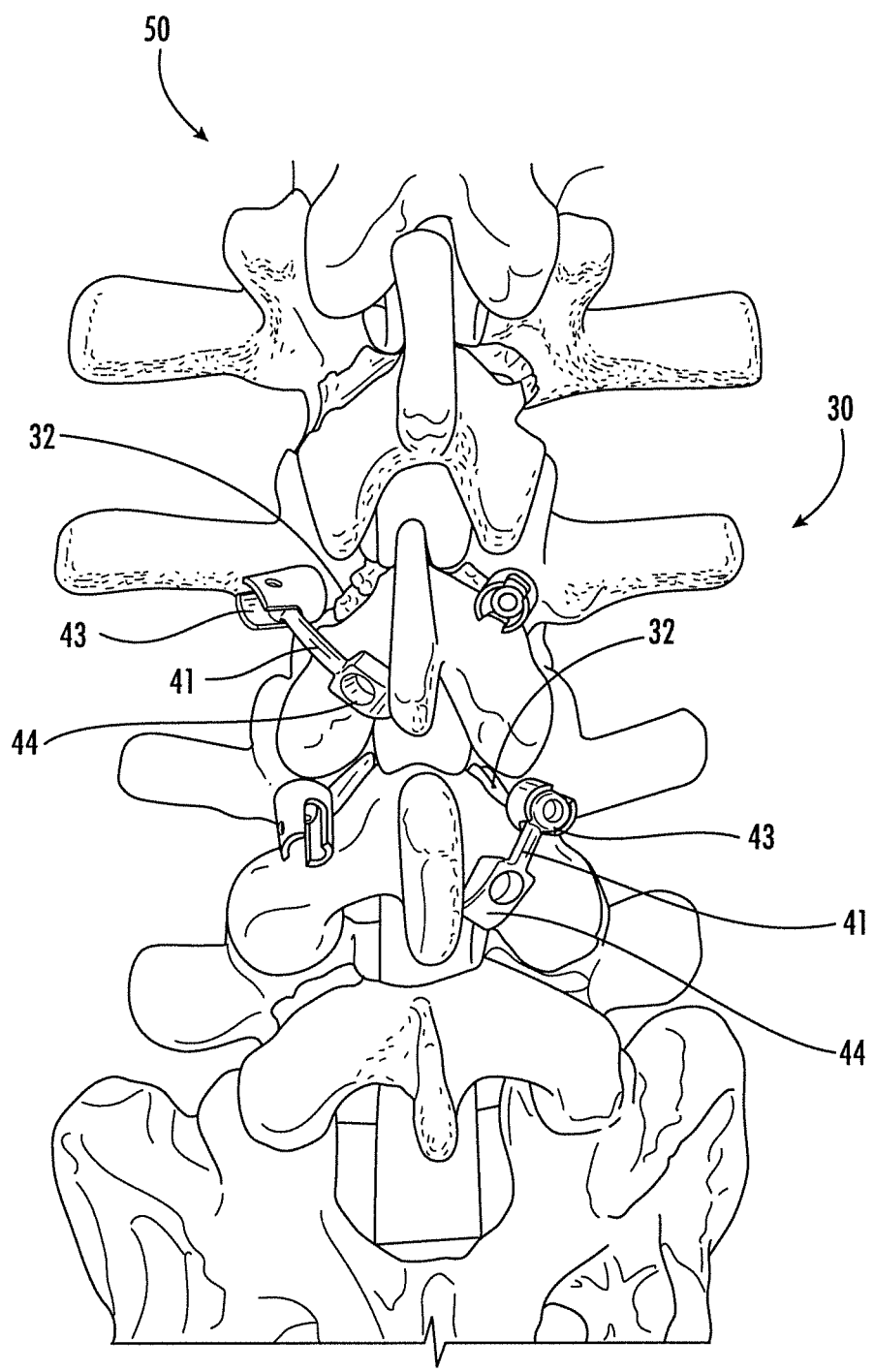
FIG. 5 is an anterior view of a spine in which a spinal stabilization system has been installed in accordance with an example embodiment.
Figure 6:
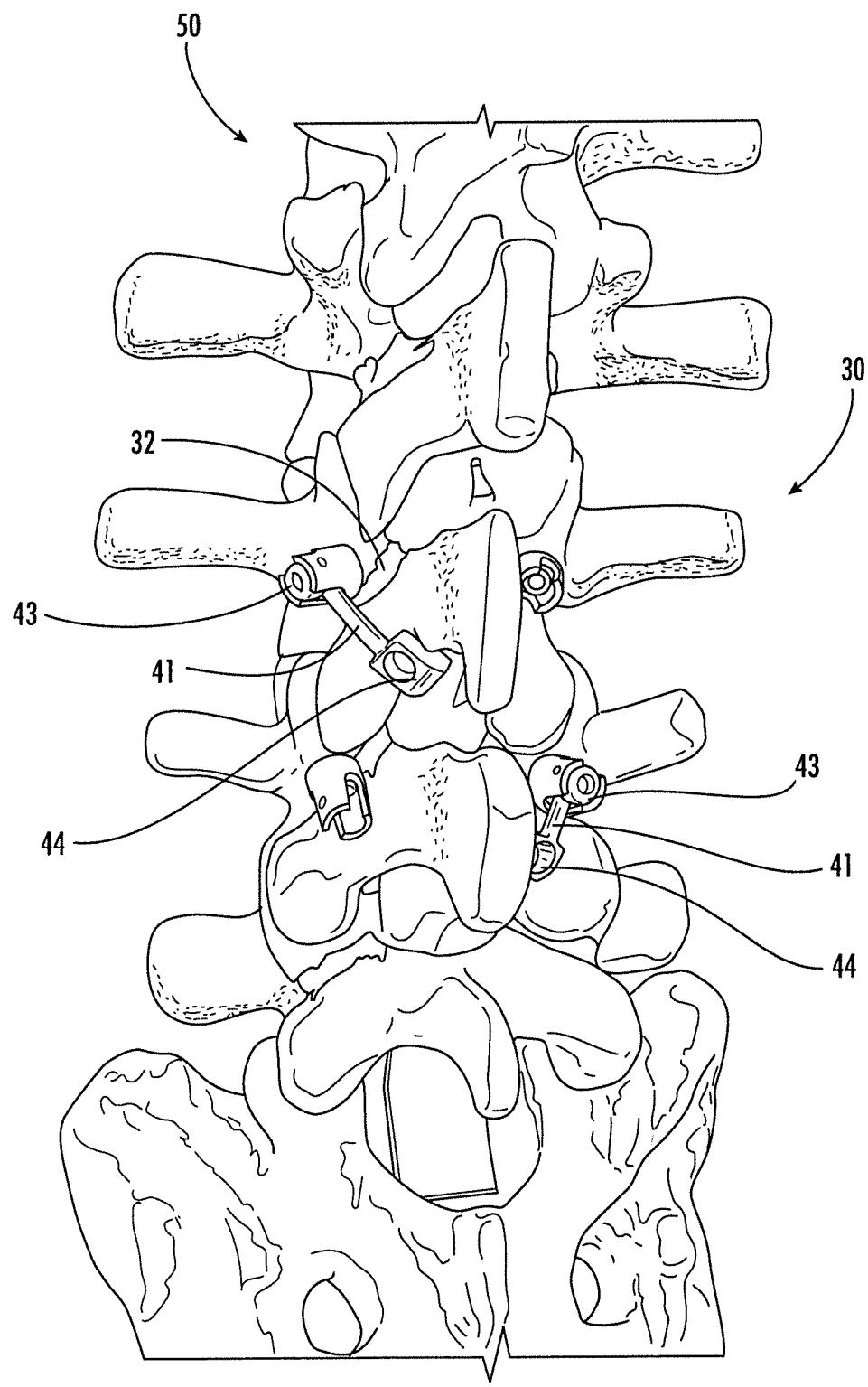
FIG. 6 is a perspective anterior view of the spine and installed spinal stabilization system of FIG. 5 from a left side of the spine.
Figure 7:
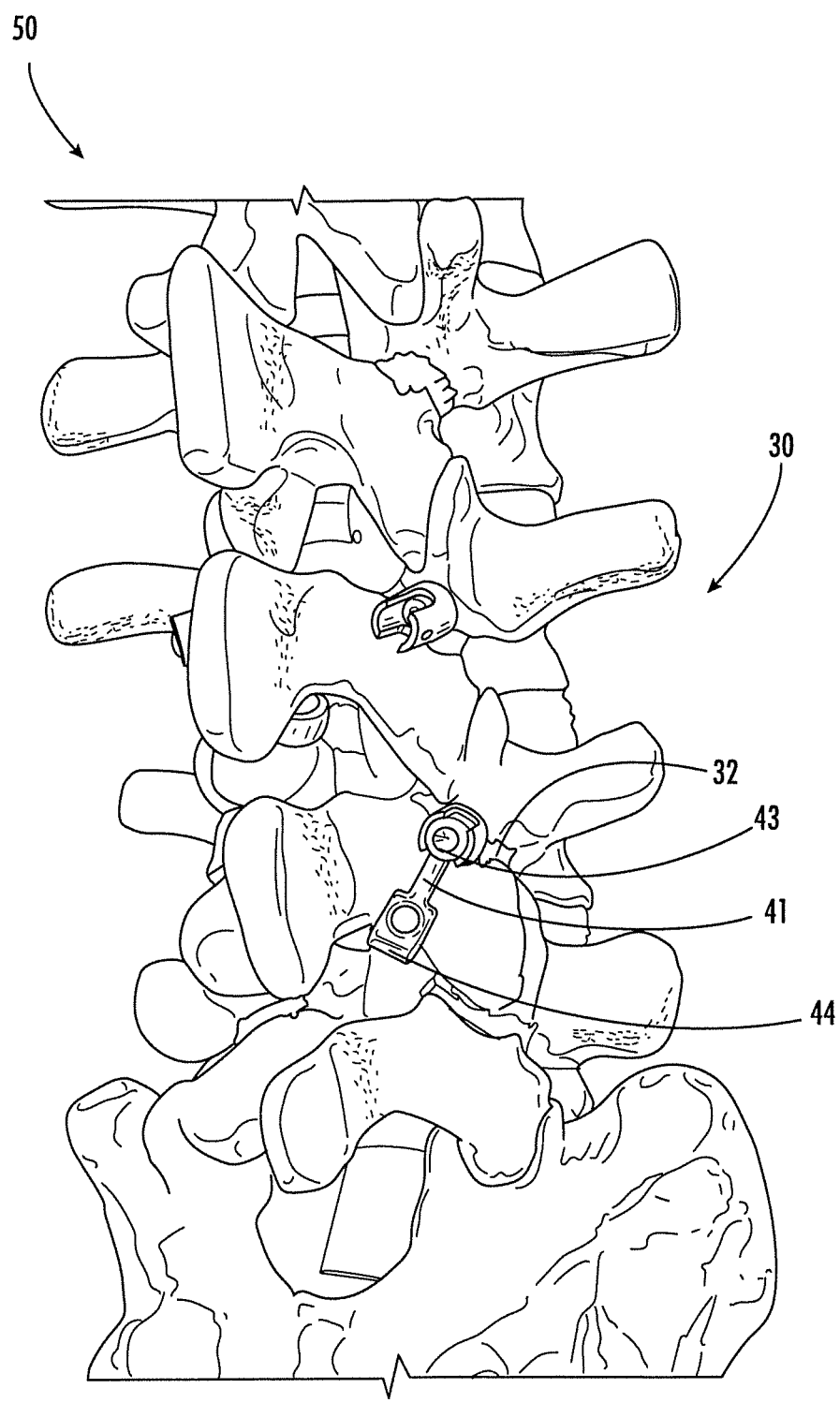
FIG. 7 is a perspective anterior view of the spine and installed spinal stabilization system of FIG. 5 from a right side of the spine.
Figure 8:
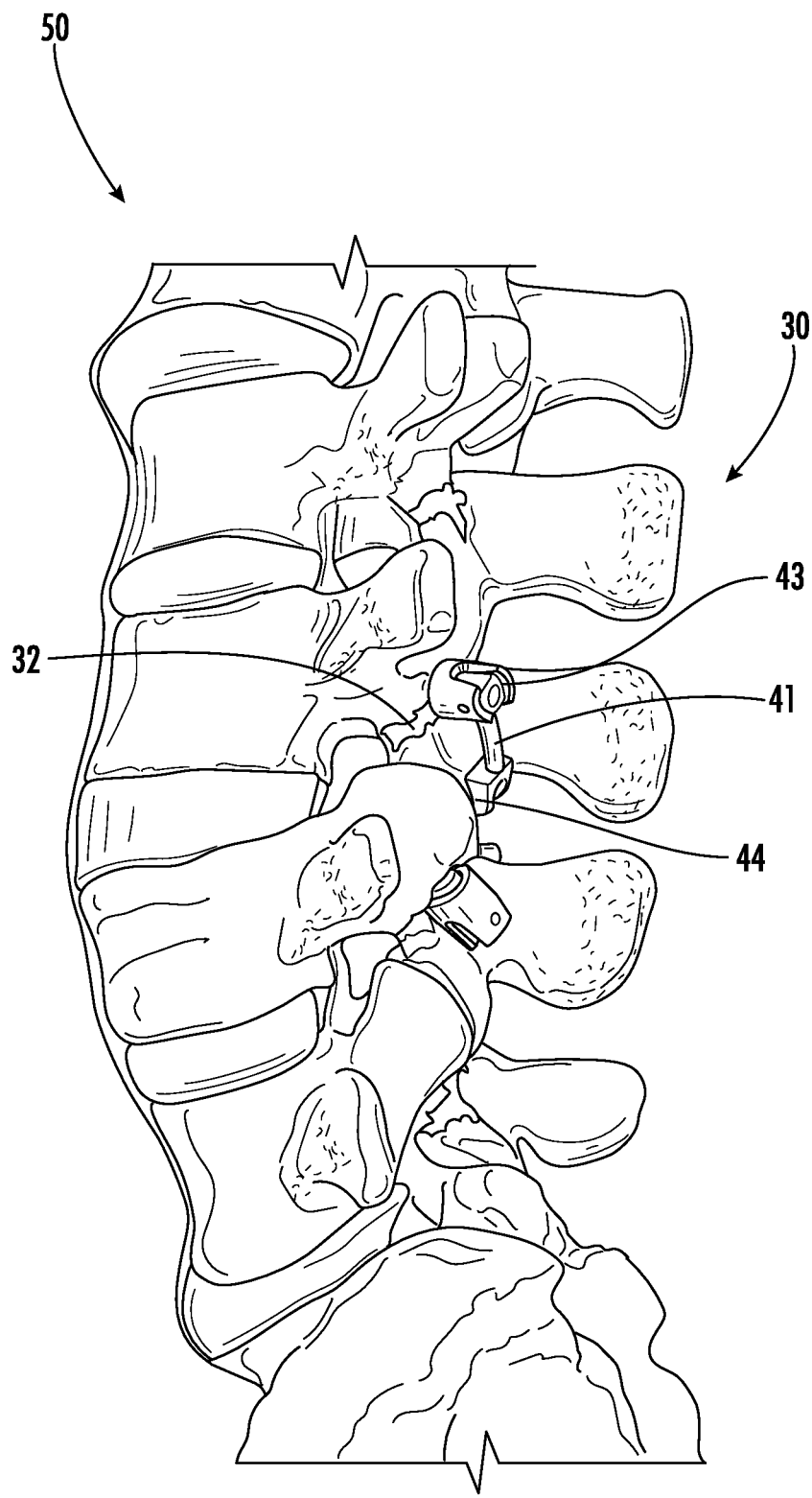
FIG. 8 is a side view of the spine and installed spinal stabilization system of FIG. 5 from a left side of the spine.
Figure 9:
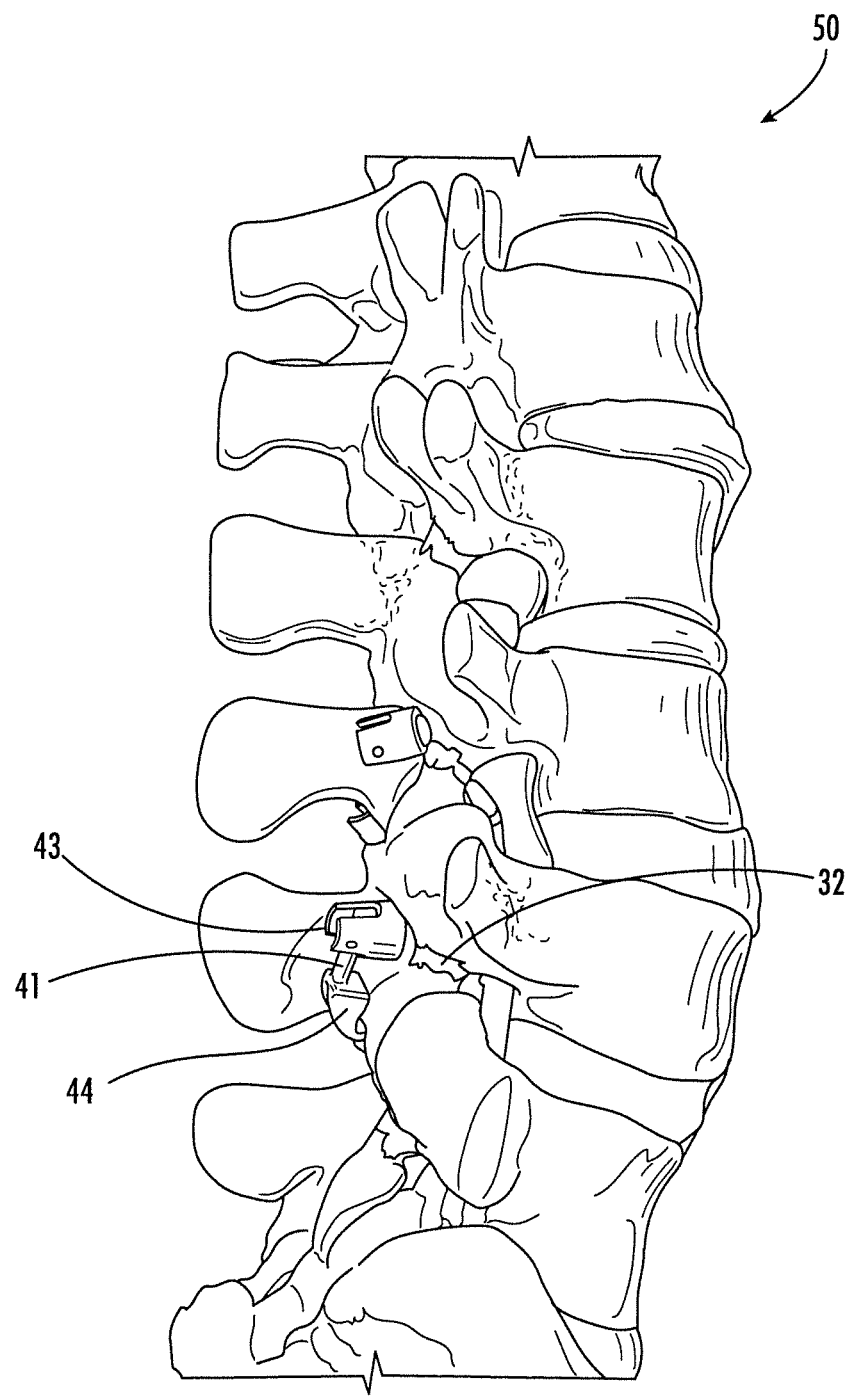
FIG. 9 is a side view of the spine and installed spinal stabilization system of FIG. 5 from a right side of the spine.
Figure 10:
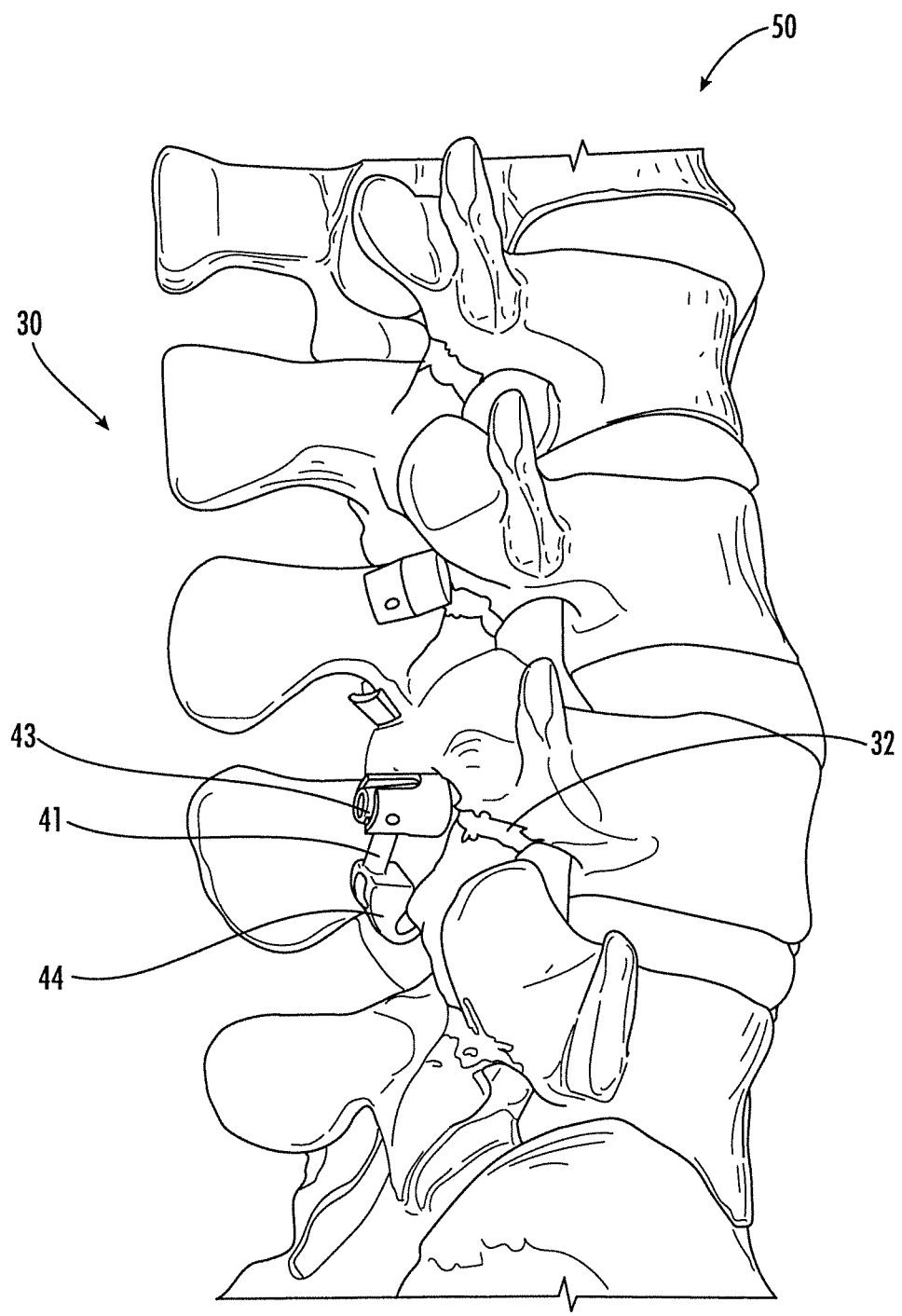
FIG. 10 is another side view of the spine and installed spinal stabilization system of FIG. 3 from a right side of the spine shown in close-up.

In the example of FIG. 1, only one pars fracture 32 is present (on the left side of the vertebra 31), but in some situations fractures will be present on each pars interarticularis 46 (bilateral fractures), as seen FIG. 3. In such cases a respective screw 42 and clamp 40 may be installed on each side of the vertebra 31 to stabilize both of the fractures 32, as shown. The implementation of FIG. 4 shows a similar installation, but with one or more small optional fixed angle screws 47 affixed to the lamina for added stability.

In the example installation of the system 30 shown in a spine 50 in FIGS. 5-10, numerous fractures across different vertebrae 31 are illustrated to demonstrate installation across multiple vertebral levels. At each level, either one pars clamp 40 may be used if a single-sided fracture 32 is present (FIG. 1), or two parts clamps 40 (or a curved clamp 40', as will be discussed further below) if a bilateral pars fracture is present (FIGS. 3 and 4).

Figure 11:
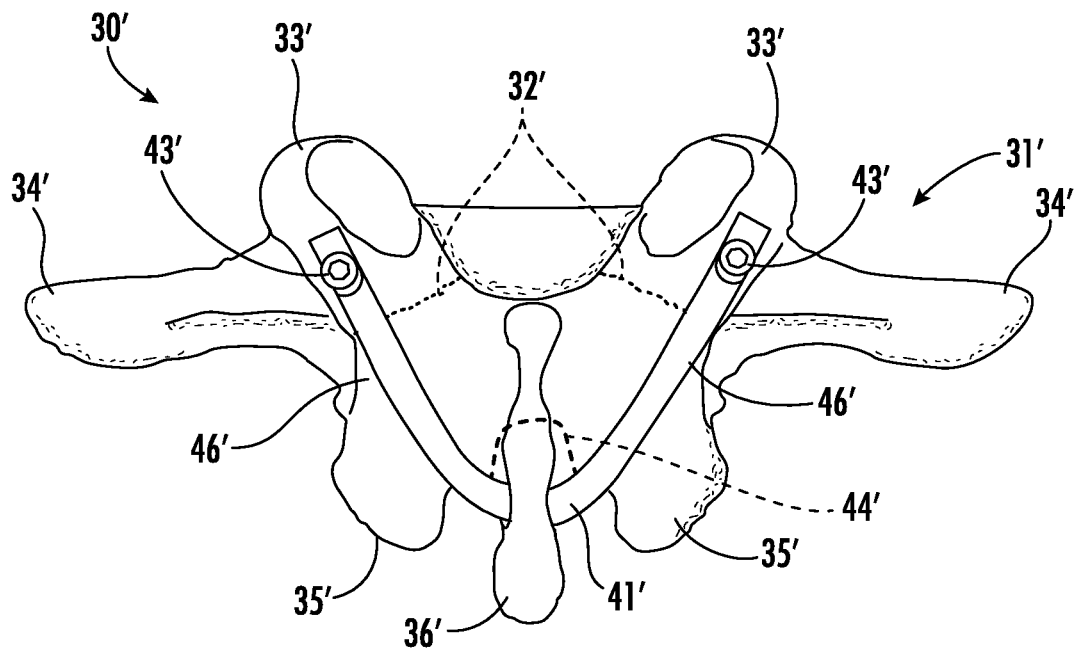
FIG. 11 is a schematic top view of a vertebra in which another example embodiment of a spinal stabilization system that has been installed for the treatment of pars interarticularis stress fractures.
Figure 12A:
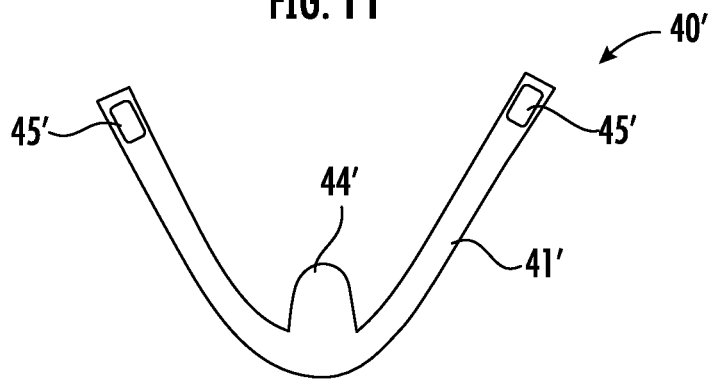
FIGS. 12A and 12B are top and side views, respectively, of the pars interarticularis clamp of the system of FIG. 11.
Figure 12B:
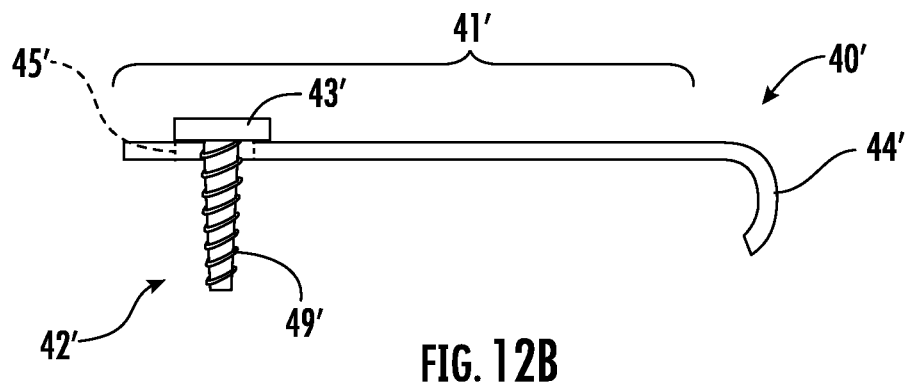

An alternative implementation of the system 30' is now described with reference to FIGS. 11-12. Here, the elongate body 41' is curved or arcuate and generally defines a "U" or wishbone shape, and the laminar hook 44' is connected at a midpoint of the elongate body (on the inside of the curve). The amount or curvature may vary depending on the geometry of the particular vertebra 31' in which the pars clamp 40' is being installed. Here, the laminar hook 44' and elongate body 41' wedge/hook under the lamina and spinous process 36, and the proximal ends are each connected to respective screw heads 43' to simultaneously secure a bilateral pars fracture 32. However, it should be noted that the pars clamp 40' may be used in cases where there is only a single-sided fracture 32, if desired, to provide rigidity and/or added stability to the opposite side of the vertebra 31 for future fracture prevention, etc.

During a surgical procedure, the surgeon may be provided with an instrumentation set having an assortment of different sizes of the "lamina hook-rods" (FIGS. 1-4), "U-shaped rods" (FIGS. 11-12), as well as small pedicle screws 42, 42' (and optionally 47) to accommodate numerous different spinal geometries. Given the uniqueness of each of these pars fractures 32, 32' and sometimes unusual congenital anatomy contributing to the injury, an additional protocol may be implemented to utilize a computerized tomography (CT) or computerized axial tomography (CAT) scan to preoperatively plan the implant exactly to the patient's unique anatomy. That is, in the case of stock hardware, appropriate sizes of hardware for a given patient may be ordered if not already in stock. Alternatively, the CT/CAT protocol allows for the creation of custom hardware crafted to a specific patient's unique anatomy. For example, using the dimensions obtained from a CT/CAT scan, a computer-generated model may be created from which custom-fit pars clamps 40, 40' may be crafted. For example, in some embodiments these custom pars clamps 40, 40' may be 3D-printed with a metal or other suitable filament. Finally, the actual surgical position of the screws 42, 42' (and optionally 47) and custom hardware can be precisely placed intraoperatively utilizing current spinal robotic technology in centers with this technology, as will be appreciated by those skilled in the art.

Figure 13:
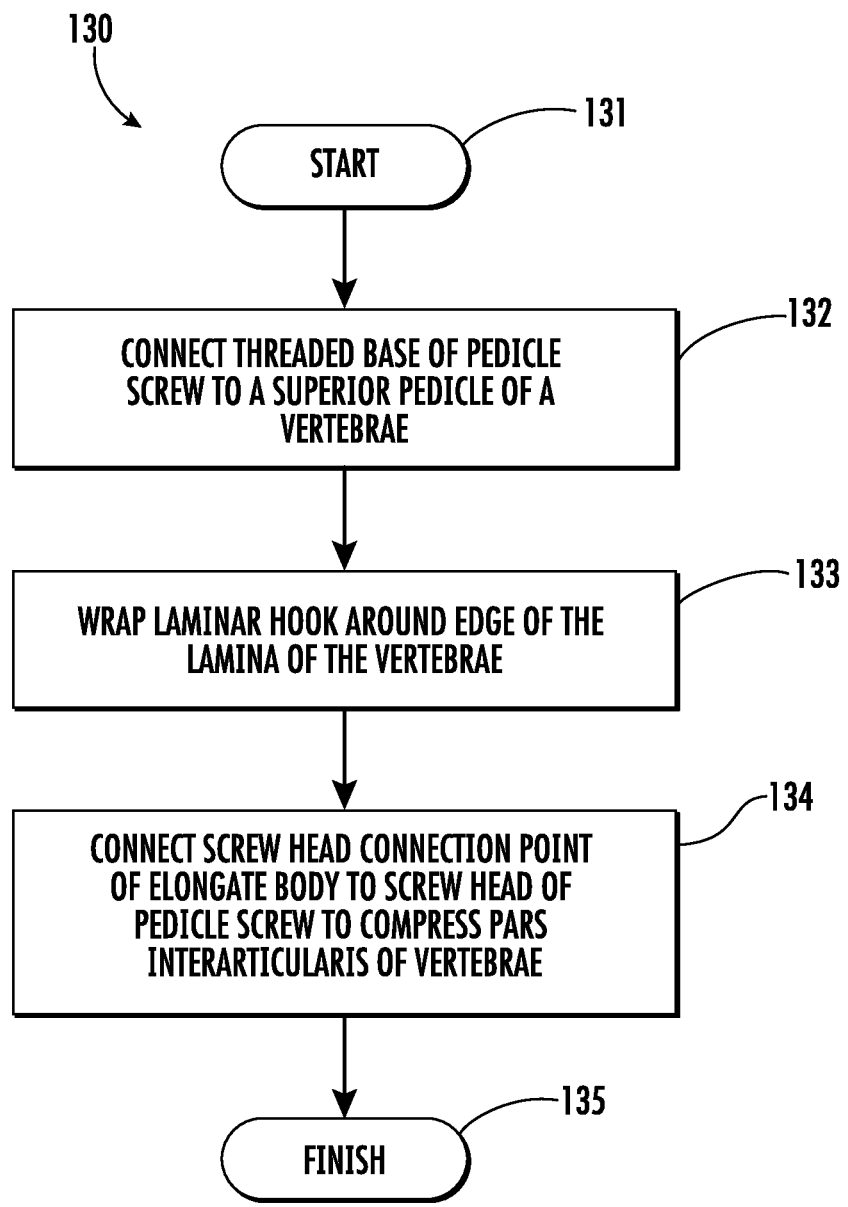
FIG. 13 is a flow diagram illustrating an example method for installing the spinal stabilization systems set forth herein.

Referring additionally to the flow diagram 130 of FIG. 13, a spinal stabilization method using the pars clamp(s) 40 or 40' is now described. Beginning at Block 131, the method illustratively includes connecting a threaded base 49, 49 of a pedicle screw 42, 42' to a superior pedicle 33, 33' of a vertebra 31, 31', with the pedicle screw comprising a screw head 43, 43' attached to the threaded base (Block 132), as discussed above. The method further illustratively includes connecting one or more pars interarticularis clamps 40, 40' to the vertebra 31, 31' by wrapping the laminar hook 44, 44' around an edge of the lamina of the vertebra 31, 31', at Block 133, and connecting a screw head connection point 45, 45' of the elongate body 41, 41' to the screw head 43, 43' of the pedicle screw 42, 42' to compress the pars interarticularis 46', 46' of the vertebra, at Block 134, as also discussed further above. It should be noted that in some installations, certain steps may be performed in different orders. For example, in some instances the screw 42 may be installed last. Optional screws 47 may also be used in some installations, as also mentioned above.

It should be noted that the above-described pars clamps 40, 40' and installation procedure may be utilized for fractures in other spinal locations, or even with other bones where suitable bone features are present to receive the hook 44, 44'. Moreover, it will also be appreciated that various sizes and shapes of the pars clamp 40, 40' may be utilized depending upon the location and type of vertebra (or other bone) where the clamp(s) is being installed.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A spinal stabilization system comprising:
   first and second pedicle screws each comprising a threaded base and an adjustable screw head having a channel therein attached to the threaded base, the treaded base of the first pedicle screw to be connected to a first superior pedicle of a vertebra and the threaded base of the second pedicle screw to be connected to a second superior pedicle of the vertebra; and
   at least one pars interarticularis clamp comprising
      a curved body having a first end to be connected to the adjustable screw head of the first pedicle screw, and a second end to be connected to the adjustable screw head of the second pedicle screw, and
      a laminar hook coupled to the curved body and configured to wrap around an edge of the lamina;
   wherein the first and second ends of the curved body are movable within the channels of the adjustable screw heads of the first and second pedicle screws, respectively, to cause the laminar hook to apply a compression force to compress the pars interarticularis of the vertebra and securable in place with the adjustable screw head.

2. The spinal stabilization system of claim 1 wherein the laminar hook is coupled to a midpoint of the curved body.

3. The spinal stabilization system of claim 1 wherein the curved body defines a U-shape.

4. The spinal stabilization system of claim 1 wherein the curved body comprises a flat body.

5. A spinal stabilization device comprising:
   a curved body having a first end to be connected to an adjustable screw head of a first pedicle screw connected to a first superior pedicle of a vertebra, and a second end to be connected to an adjustable screw head of a second pedicle screw connected to a second superior pedicle of the vertebra; and
   a laminar hook coupled to the curved body and configured to wrap around an edge of the lamina;
   wherein the first and second ends of the curved body are movable within the channels of the adjustable screw heads of the first and second pedicle screws, respectively, to cause the laminar hook to apply a compression force to compress the pars interarticularis of the vertebra and securable in place with the adjustable screw head.

6. The spinal stabilization device of claim 5 wherein the laminar hook is coupled to a midpoint of the curved body.

7. The spinal stabilization device of claim 5 wherein the curved body defines a U-shape.

8. The spinal stabilization device of claim 5 wherein the curved body comprises a flat body.

9. A spinal stabilization method comprising:
   connecting a threaded base of a first pedicle screw to a first superior pedicle of a vertebra and a second threaded base of a second pedicle screw to a second superior pedicle of the vertebra, each of the first and second pedicle screws comprising an adjustable screw head having a channel therein attached to the respective threaded base; and connecting at least one pars interarticularis clamp comprising a curved body defining first and second ends and a laminar hook coupled to the curved body to the vertebra by wrapping the laminar hook around an edge of the lamina of the vertebra, moving the first and second ends of the curved body within the channels of the first and second adjustable screw heads, respectively, to compress the pars interarticularis of the vertebra, and securing the first and second ends of the elongate body in place with the adjustable screw heads of the first and second pedicle screws, respectively, after compressing the pars interarticularis.

10. The method of claim 9 wherein the laminar hook is coupled to a midpoint of the curved body.

11. The method of claim 9 wherein the curved body defines a U-shape.

12. The method of claim 9 wherein the curved body comprises a flat body.

\* \* \* \* \*